United States Patent [19]

Parsy et al.

[11] Patent Number: 5,714,677
[45] Date of Patent: Feb. 3, 1998

[54] DEVICE FOR AUTOMATICALLY INJECTING SOLUBILIZED OR DILUTED SUBSTANCES

[76] Inventors: Philippe Parsy, 14 boulevard Anatole France, F-86000 Poitiers, France; Marc André Lefebvre, Maupertuis Coulombiers, F-86600 Lusignan, France

[21] Appl. No.: 679,805

[22] Filed: Jul. 15, 1996

Related U.S. Application Data

[63] Continuation of PCT/FR95/00011 Jan. 5, 1995.

[30] Foreign Application Priority Data

Jan. 14, 1994 [FR] France .................................. 94 00388

[51] Int. Cl.$^6$ ........................................................ G01N 30/24
[52] U.S. Cl. .......................... 73/23.41; 73/863.11; 95/89; 96/105; 422/78
[58] Field of Search .................. 73/23.41, 23.35, 73/863.11, 863.12, 864.81, 23.42; 432/128, 152, 155; 95/89; 96/105, 106; 422/78; 436/157, 199

[56] References Cited

U.S. PATENT DOCUMENTS

| | | | |
|---|---|---|---|
| 3,173,762 | 3/1965 | Varadi et al. | 73/23.41 X |
| 3,498,107 | 3/1970 | Kim et al. | 73/23.41 X |
| 3,759,107 | 9/1973 | Fox et al. | 73/863.11 |
| 4,824,790 | 4/1989 | Carangelo et al. | 436/157 |
| 4,849,179 | 7/1989 | Reinhardt et al. | 95/89 X |
| 5,009,591 | 4/1991 | Watanabe | 432/128 |
| 5,065,614 | 11/1991 | Hartman et al. | 73/23.35 |

FOREIGN PATENT DOCUMENTS

| | | |
|---|---|---|
| 0 027 601 | 4/1981 | European Pat. Off. . |
| 57-182164 | 11/1982 | Japan . |

OTHER PUBLICATIONS

"An Autosampler with a Short Transfer Line for *Curie* Point Pyrolysis Capillary Gas Chromatography", *Journal of High Resolution Chromatography*, vol. 16, No. 6, 1993, pp. 353–357.

"Temperature Rise Time and True Pyrolysis Temperature in Pulse Mode Pyrolysis Gas Chromatography", *Analytical Chemistry*, vol. 44, No. 1, Jan. 1972, pp. 38–42.

*Primary Examiner*—Michael Brock
*Attorney, Agent, or Firm*—Young & Thompson

[57] ABSTRACT

The invention concerns a device for automatically injecting substances solubilised or diluted in a solvent for a gaseous phase chromatographic analysis column (14), wherein it includes a concentration/calcination chamber (10), a vaporization chamber (12) in contact with the chromatographic column (14), a sample support (16) moving in the concentration/calcination chamber between a first position in which the sample is in the concentration/calcination chamber and a second position in which the sample is in the vaporization chamber, as well as a system (18) for scavenging the two chambers with a vector gas.

10 Claims, 5 Drawing Sheets

DEVICE FOR AUTOMATICALLY INJECTING SOLUBILIZED OR DILUTED SUBSTANCES

This application is a continuation of co-pending international application PCT/FR95/00011 filed Jan. 5, 1995, which designated the United States.

FIELD OF THE INVENTION

The present invention concerns a device for automatically injecting solubilized or diluted substances.

BACKGROUND OF THE INVENTION

In fact, analysis laboratories use gaseous phase chromatography to determine the composition and presence of certain bodies.

Gaseous phase chromatography is carried out with the aid of a specific column able to separate the various compounds on a substrate.

These devices function automatically and, by means of an information processing, provide fully clear results extremely quickly.

These chromatographic analysis devices are also used at extremely high rates.

These highly elaborate devices are expensive and their depreciation can only be effected by an extensive use.

Therefore, it is necessary, not only to provide an improved chromatographic device, but also a device for introducing the substance sample to be analyzed into the chromatographic column. It is also known that these introduction means limit the efficiency of chromatographic devices.

Existing means offer an automated introduction at the right of the chromatographic column of a support, namely a glass needle drop of the liquid phase substance being placed at the extremity of said support before being introduced.

This placing is carried out with the aid of a syringe since the glass needle is manoeuvered manually.

This needle is placed in a heated chamber which provokes the vaporization of the volatile compounds of the substance placed at the extremity of the needle.

There is a first restraint linked to this device: it is necessary to continuously heat this chamber so that it has a stabilized temperature. In addition, during analyses, it is possible to observe a crushing of this glass needle which prejudices the analysis sensitivity of the device.

Also, the operator is obliged to clean or indeed regularly change this needle which, apart from the material costs, involves handling costs and operating losses due to the immobilization of the analysis means.

Furthermore, the manual phase for placing the sample is in itself a significant restraint to be taken into account when operating this type of analysis device. In fact, reproducibility is of necessity altered. The task is no longer justified and personnel need to be continually immediately close to these analyses means so as to be able to intervene and place the substance sample on the glass needle once the preceding analysis has ended.

SUMMARY OF THE INVENTION

The object of the present invention is to fully automate the placing of samples, the injection means and their cleaning so as to allow a continuous use of the analysis device with improved reproducibility whilst freeing personnel for carrying out more important tasks.

To this effect, the device for automatically injecting substances solubilized or diluted in a solvent, as provided in the present invention and applicable to gaseous phase chromatographic columns, is characterized in that it includes a concentration/calcination chamber, a vaporization chamber in link with the chromatographic column, a sample support able to move vertically in the concentration/calcination chamber between a first position where the sample is in the concentration/calcination chamber, and a second position where the sample is in the vaporization chamber, as well as a system for having the two chambers scavenged by a vector gas.

According to another characteristic of the invention, the sample support includes a mobile base on which a heating filament and electric power units are mounted connected to said filament, and the concentration/calcination and vaporization chambers each include electric power units for entering into contact with the electric power units of the base when said base is in either chamber.

According to one preferred embodiment, the electric power units can have their power adjusted.

The disposition of the automatic injection device of the invention is provided so that the concentration/calcination chamber is orientated vertically so as to receive on sliding the base subjected to gravity and mobile between an upper position and a low position. This chamber also includes means for locking and unlocking the base in the upper position.

This base may be a soft-iron core with an electromagnet as a locking/unlocking device, this electromagnet being disposed at the upper portion of the concentration/calcination chamber.

The scavenging system includes a first gas intake stitching opening between the concentration/calcination and vaporization chambers, a second gas outlet stitching opening outside the concentration/calcination chamber, this second stitching comprising a first channel and a second channel, the first channel with a slight flow being equipped with a nozzle and the second channel with a high flow with an electrovalve.

According to one embodiment, the disposition of the automatic injection device of the invention is such that the second stitching is situated immediately under the base when the latter is in the upper position.

The concentration/calcination chamber also includes an orifice for introducing the upper portion of the needle above the base when the latter is in the upper position and the base includes an opening hole orientated vertically coaxial to the introduction orifice so as to enable the needle of the syringe to pass through the base and thus authorize access to the filament and distribution of the sample.

According to a particular disposition of the second embodiment, the concentration/calcination chamber includes an upper plate and a lower plate, two upper and lower bases, two upper and lower tubes made of a nonconducting material, such as glass, two upper and lower metallic electrodes each including two superbores for receiving firstly the upper and lower tubes and secondly an intermediate tube, also made of a transparent nonconducting material, especially glass.

BRIEF DESCRIPTION OF THE DRAWINGS

The invention is now described hereafter with reference to the accompanying figures.

DESCRIPTION OF THE PREFERRED EMBODIMENT

Figure 1:
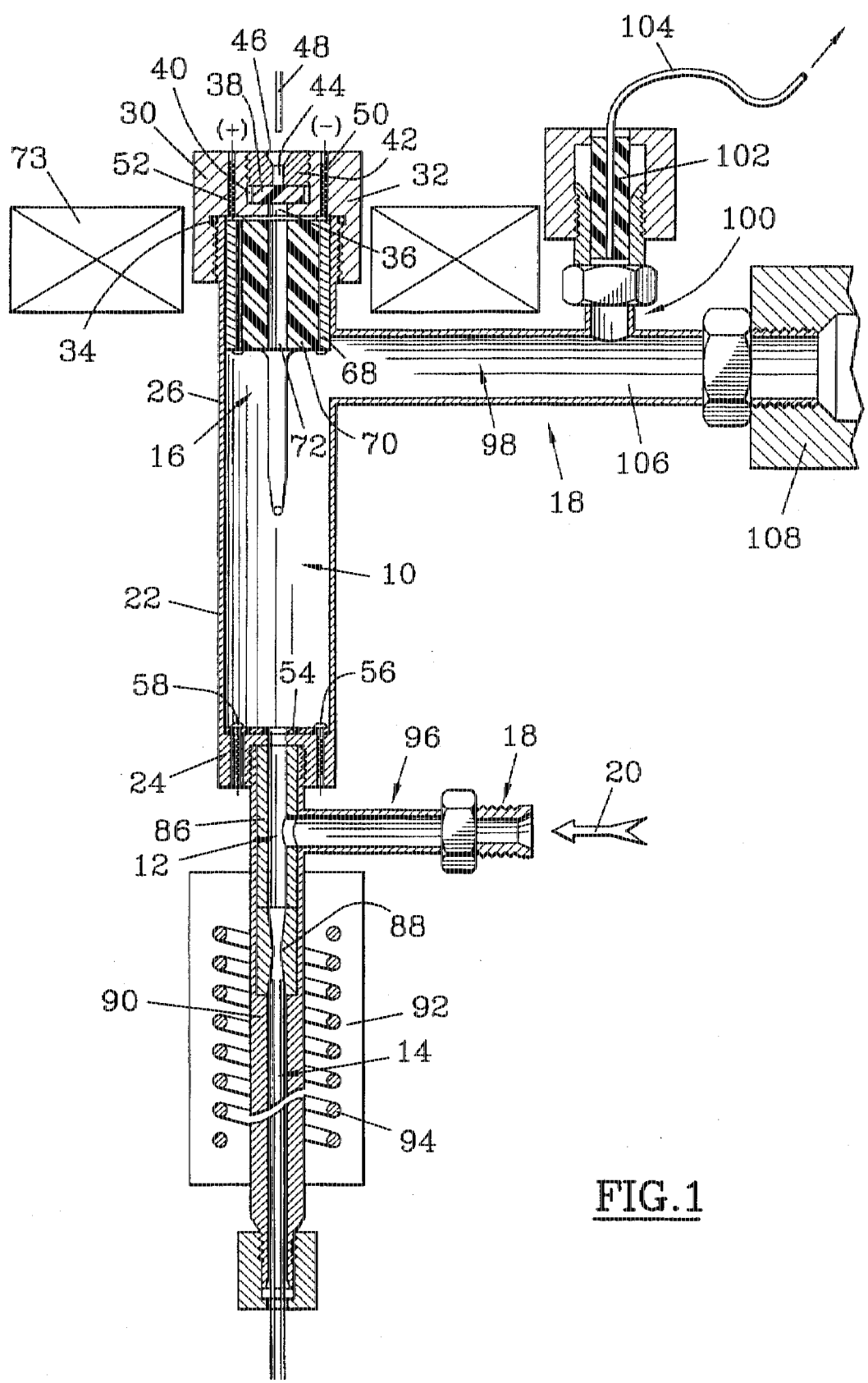
FIG. 1 is a general cutaway diagrammatic view of a first embodiment of the automatic injection device of the invention with the mobile base in the upper position.

FIG. 1 shows a concentration/calcination chamber 10, a vaporization chamber 12 in link with a gaseous phase chromatographic column, a sample support 16 able to move vertically in the concentration/calcination chamber, as well as a system 18 for scavenging the concentration/calcination and vaporization chambers by a vector gas 20.

The concentration/calcination chamber 10 includes a cylindrical tube 22 whose longitudinal axis is orientated vertically and whose lower extremity 24 is connected to the vaporization chamber 12 and to the chromatographic column 14, whereas the upper extremity 26 includes an injection head 30.

This injection head includes a cover 32 screwed onto the upper extremity 26 with a gasket 34.

This cover 32 includes an injection hole 36 sealed off by a polymer washer 38 disposed in a tapped superbore 40 and intended to receive a screwed stopper 42 equipped with a pipe 44 opening onto the upper face of the washer 38 and fitted at its upper portion with a funnel-shaped element 46 for receiving and guiding a needle 48 of a syringe (not shown).

This cover 32 is also equipped with two electric power units 50, 52 connected to the + and − poles of a generator, these terminals projecting onto the lower face of the cover in direct contact with the inside of the concentration/calcination chamber 10.

Figure 2:
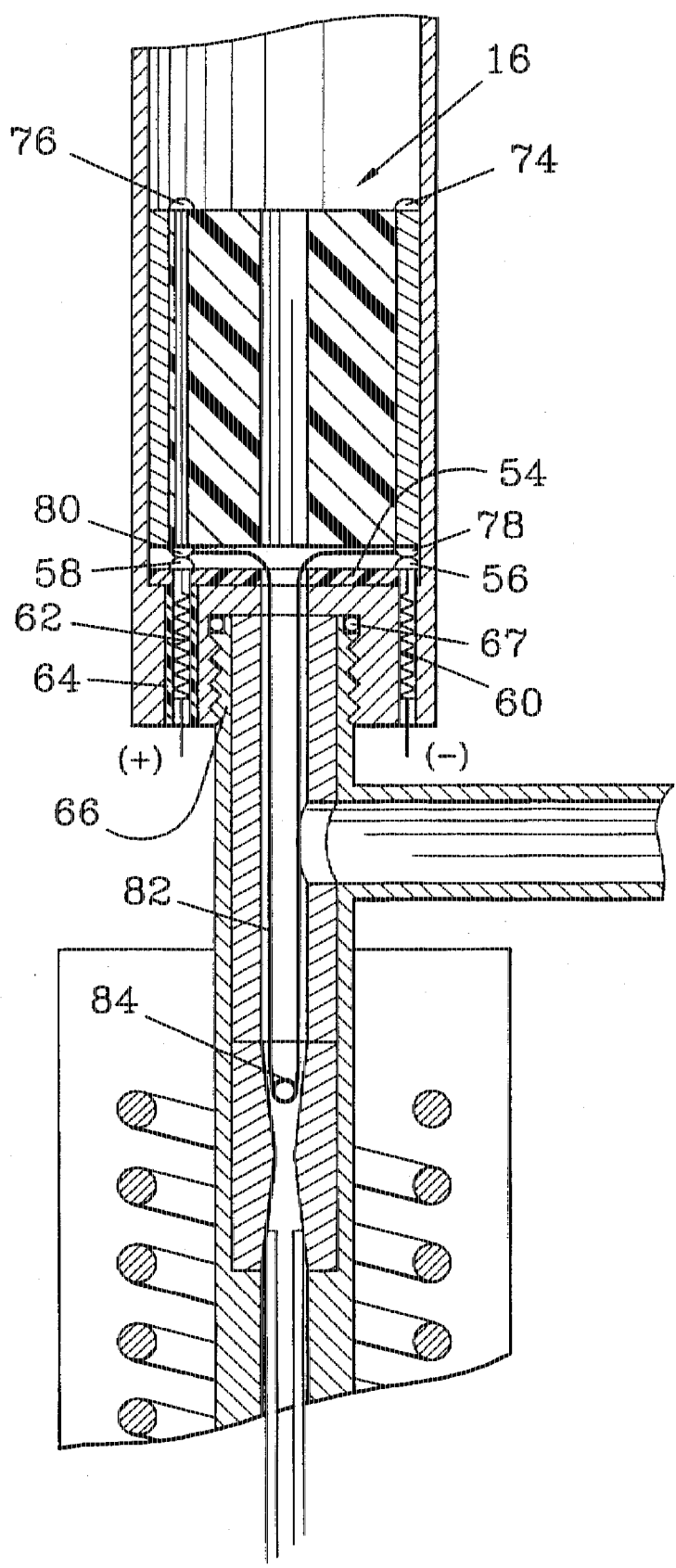
FIG. 2 is a detailed view of the injection device of FIG. 1 when the mobile base is in the lower position, FIG. 3 which includes the stages A, B, C, D, and E, is a synoptic diagram of the functioning of the automatic injection device of the invention.
Figure 3A:
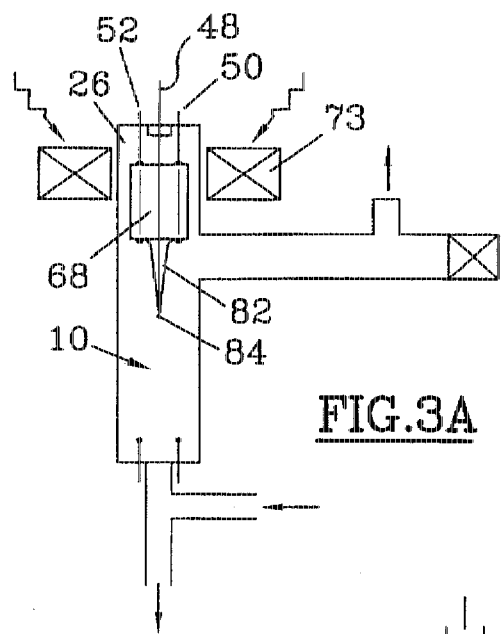
Figure 3B:
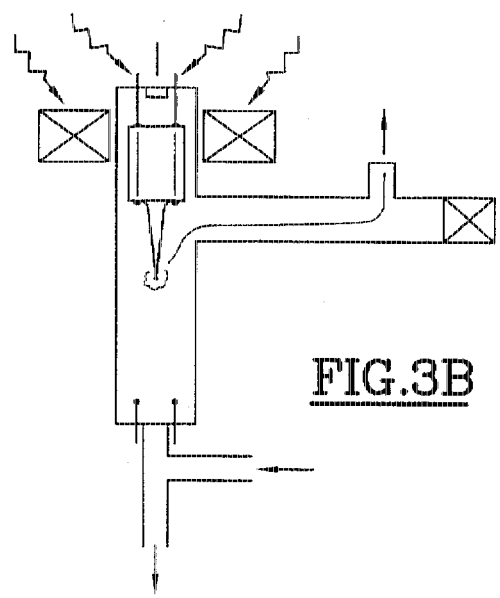
Figure 3C:
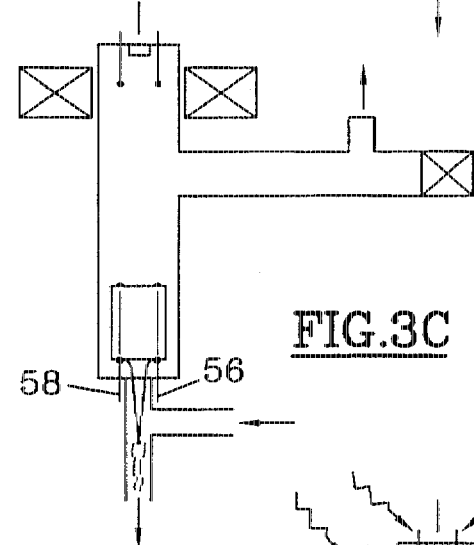
Figure 3D:
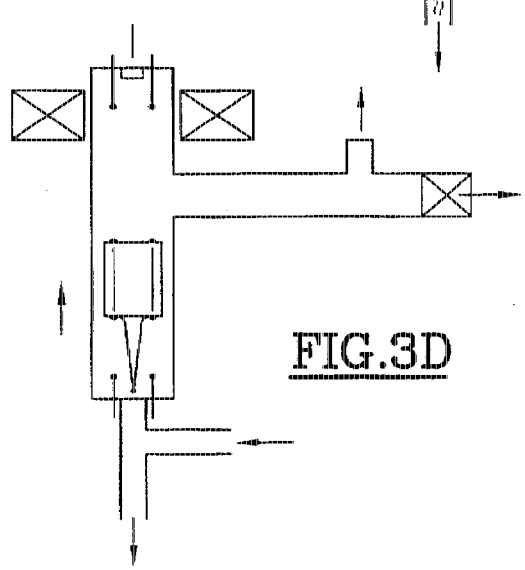
Figure 3E:
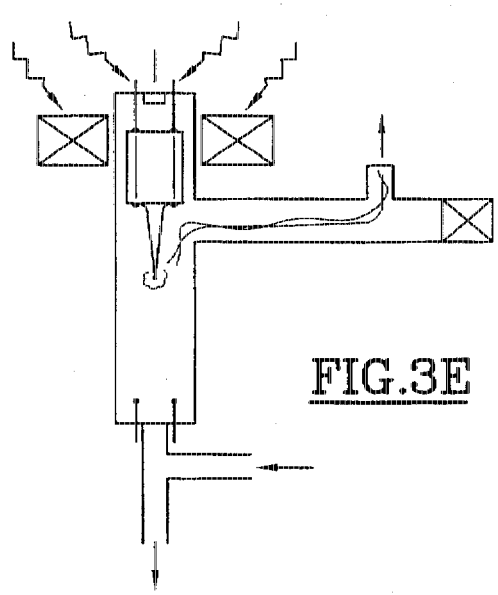

The lower extremity 24 of the concentration/calcination chamber 10 includes an isolation washer 54 at its lower portion traversed by two terminals 56 and 58 respectively connected to the − and + poles respectively of a current generator and mounted on springs 60 and 62 respectively working on compression (see FIG. 2).

A nonconducting sleeve 64 is provided at the periphery of the terminal 58 connected to the positive pole of the current generator.

The lower portion 24 is screwed into the extremity 66 of the vaporization chamber 12 and a joint 67 ensures imperviousness.

The mobile sample support 16 includes a metallic base 68 containing a nonconducting core 70 fitted with a central hole 72, the outer shape of the base corresponding to the nearest clearance to the shape of the concentration/calcination chamber.

This base, which can be seen more easily on FIG. 2, is equipped with upper 74 and 76 and lower 78 and 80 electric terminals electrically connected two by two.

Furthermore, a filament 82 is integral with this base and more particularly its extremities are integral with the lower electric terminals 78 and 80 of the mobile base.

This filament 82 has a pointed shape and has a winding 84 at its extremity.

The mobile sample support 16 further includes an electromagnet 73 disposed at the periphery of the upper extremity 26 of the concentration/calcination chamber 10, the power of this electromagnet being such that the electromagnetic forces generated keep the base 68 in a stable upper position against its own weight.

The known type of vaporization chamber 12 mainly includes a tubular section 86 which opens with a throat 88 in the chromatographic column 14 disposed in a heating chamber 92 equipped with resistors 94.

The scavenging system includes a first stitching 96 allowing the gas 20 to enter the vaporization chamber 12 between the concentration/calcination chambers 10 and the chromatographic column 14.

This scavenging system is completed by a second gas outlet stitching 98 opening outside the concentration/calcination chamber 10 immediately below the base 68 when the latter is in the upper position, as shown on FIG. 1.

A second stitching 98 includes a first channel 100 equipped with a nozzle 102 opening into a tube 104 and a second high flow channel 106 equipped with an electrovalve 108.

The functioning of this first embodiment is described hereafter in detail, especially with regard to the synoptic diagram of FIG. 3.

In stage A, the electromagnet 73 is fed and keeps the base 68 in its upper position, that is in front of the extremity 26 of the concentration/calcination chamber 10, the upper terminals 74 and 76 of this base cooperating with the electric power units 50 and 52 provided in the cover 32.

The earth (negative terminal) is embodied by the metallic material constituting the base 68 so that the upper 74 and lower 78 terminals are at the same potential.

The terminals 76 and 80 are also at the same potential, positive in this case since they are interconnected through the nonconducting core 70.

The chromatographic column is on stand-by and the scavenging system is fed with a relatively low flow by the first stitching 96, the gas 20 circulating upwards through the concentration/calcination chamber 10, then through the second stitching 98 so as to be evacuated by the first channel 100 through the nozzle 102 as far as into the evacuation pipe 104, the electrovalve 108 being closed.

This vector gas is selected as being suitable for the substance to be analyzed, this choice not forming part of the present invention and able to be effected by a man skilled in the art.

With the electrovalve closed, the needle 48 of a syringe (not shown) is introduced through the hole 44 by virtue of the funnel shape 46 which ensures guiding up to the extremity of the filament 82 and more particularly up to the loop 84 after having traversed the elastomer sealing pellet 38.

This introduction of the needle of a syringe can be carried out by a known type of automaton and does not form part of the invention.

During this stage A, the syringe is activated so as to place by means of this needle a drop of the diluted or dissolved substance on the loop 84 of the filament 82 which it adheres by means of the capillary attraction forces.

At stage B, the electromagnet 73 is still fed so as to keep the base 68 in its upper position, the needle 48 having been withdrawn and the vector gas kept at a low rate.

If the vapor tension of the solvent is not slight enough at working temperature, a current by means of the electric power units 50 and 52 is made to pass through the upper terminals 74 and 76 which themselves feed the terminals 78 and 80 and allow for a circulation of current through the filament 82. The intensity is calculated so that, having regard to the section of the filament, the latter rises when the temperature goes up and provokes the evaporation of the solvent without degrading the substance carried.

The vector gas current propels the solvent through the nozzle 102.

In stage C, the feeding of the electromagnet 73 is cut which provokes the fall via gravity of the mobile base 68 down to its lower position and the penetration of the filament 82 into the vaporization chamber 86, the base being in support on the electric power units 56 and 58, the springs 60 and 62 dampening the fall of the base.

The electric terminals 78 and 80 of the base are then connected to the power units 56 and 58.

The loop 84 of the filament is located immediately above the chromatographic column whose walls 90 are shown on FIG. 2.

The vector gas current 20 is orientated more particularly towards the chromatographic column as the base and the filament take up space in the lower portion 24 of the concentration/calcination chamber.

The electric power units 60 and 62 allow a current to be made to pass through the filament 82 which is heated to a temperature higher than the one which provoked evaporation of the solvent so as to provoke the volatilization of the concentrated substance and fractionating on the phase of the chromatographic column.

The heating power is generated and calculated according to the substance to be analyzed.

The chamber 92 is also heated so as to reach the adequate temperature according to the nature of the substances.

The temperatures, type of vector gases, the heating periods and all the control parameters are currently used and well known by the men skilled in the art carrying out gaseous phase chromatography.

Accordingly, there is no need to give analysis examples.

Once chromatography has been carried out, stage D makes it possible to replace the base in its upper position by opening the electrovalve 108 and injecting a high flow vector gas 20.

Thus, the gas circulation provokes the movement of the base 68 along the arrow of stage D at the same time as a scavenging of both the vaporization chamber and the concentration/calcination chamber.

During stage E, the mobile base, having arrived at the upper position, is kept there by the electromagnet which is refed with electric energy.

At the same time, the electrovalve is closed during this stage.

During this stage E, which corresponds to cleaning of the filament 82, the electric terminals 74 and 76 are fed by a high-powered electric current so as to heat the filament to a high temperature and provoke the calcination of the substances which could have existed on the filament.

In this case, the circulation of the vector gas is reduced to a slight flow so as to simply evacuate the gases generated by calcination with an extremely slight amount of substance.

The automatic injection device is then brought back to its initial position shown on stage A so as to be ready for a new cycle.

Figure 4:
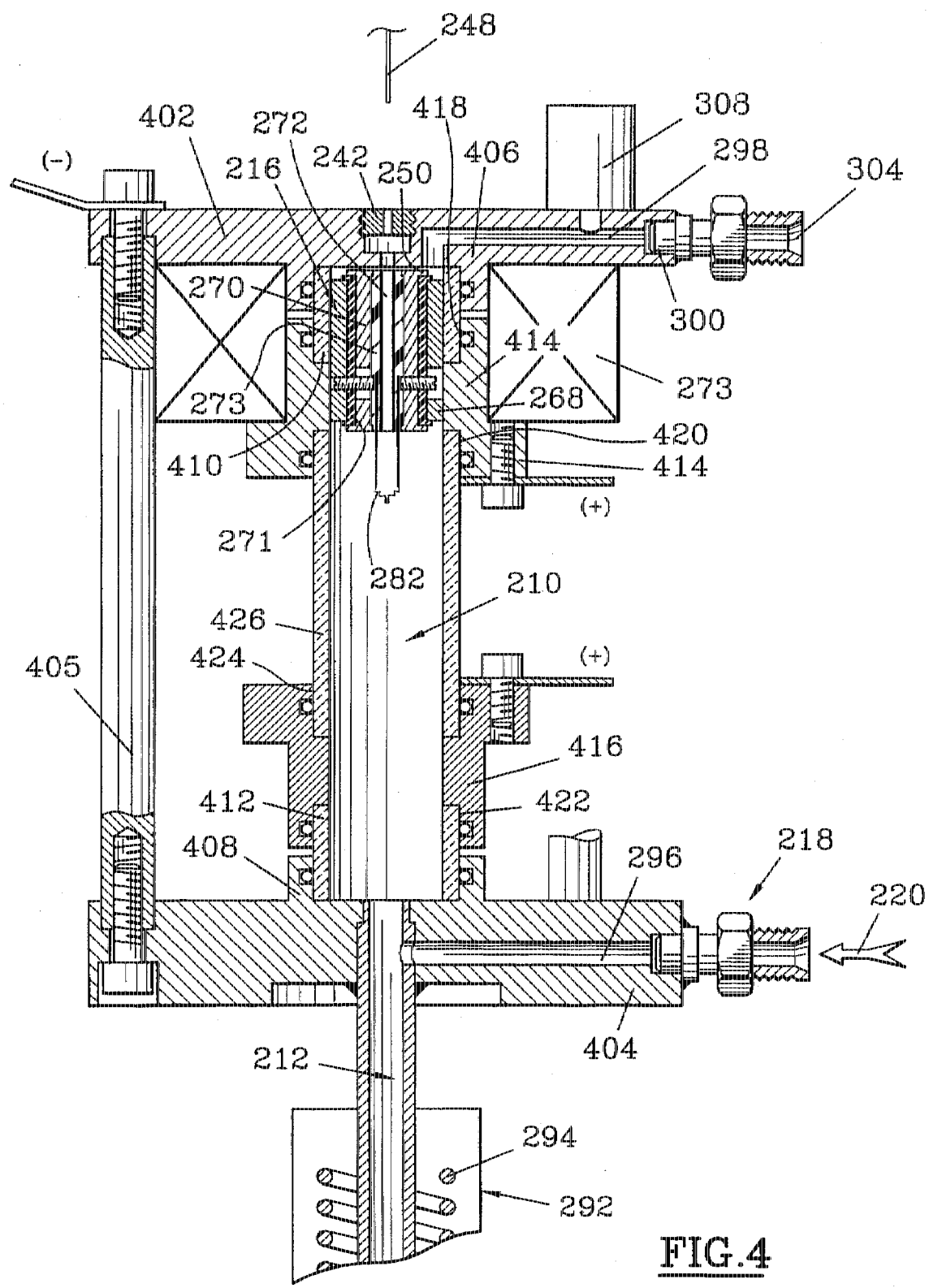
FIG. 4 is a view of a second embodiment of the injection device of the invention.

The present invention also concerns an improved industrial embodiment variant shown on FIG. 4. The elements identical to those of the main embodiment are given the same number plus 200.

The frame of the device includes an upper plate 402 and a lower plate 404 interconnected by tie rods 405. Each of these plates includes a cylindrical base 406 and 408 machined with the plates and orientated in relation to them. These two bases 406 and 408 are provided to receive the concentration/calcination chamber 210.

This chamber includes an upper tube 410 and a lower tube 412 both cooperating with the bases 406 and 408 respectively via the simple nesting of toric joints ensuring imperviousness. These joints are more particularly selected as being made of a material commercialized under the name VITON.

Two upper 414 and lower 416 cylindrical metallic electrodes are each fitted with two superbores 418, 420 and 422, 424, the superbores 418, 422 being provided to be nested respectively on the upper tube 410 and on the lower tube 412.

The other two superbores 420 and 424 are provided to receive via nesting the extremities of an intermediate tube 426. Joints of the same type as previously are provided to ensure imperviousness.

An electromagnet 273 is disposed at its upper position immediately below the upper plate 402. The lower plate 404 is fitted with an internal pipe 296 for feeding with vector gas 220. A vaporization chamber 212 is secured to this lower plate with a peripheral oven 292 fitted with a set of resistors 294 identically as in the embodiment of FIG. 1.

The upper plate 402 is fitted with an internal pipe 298 connected to an evacuation pipe 304 with a nozzle 300 with a pre-adjusted flow for a given pressure.

This upper plate is also equipped with an electrovalve 308, identical to the electrovalve 108 of the first embodiment, inserted on the internal pipe 298.

The mobile sample support 216 includes four concentric portions: an outer ring 268 made of a conductive material, a first ring 271 made of a non-conducting material, an internal ring 270 made of a conductive material, and a second ring 273 made of a non-conducting material fitted with a central bore 272. These four rings are rotary-immobilized with respect to one another.

The second ring 273 made of a non-conducting material includes two blind holes for receiving the crimped thimbles on the extremities of the wire comprising the filament 282. Two locking screws are provided to screw into two internal screw threads respectively fitted in the internal ring and in the outer ring. The internal ring includes a hole for passage of the screw cooperating with the outer ring so as to avoid any electric contact between the two rings and the outer ring includes a hole for passage of the screw cooperating with the internal ring so as to also avoid any electric contact between the two rings.

The first ring made of a non-conducting material is fitted with suitably adapted holes to allow for the screwing of the two screws in the internal ring.

The outer diameter of the mobile sample support is equal to the nearest operating play to the internal diameter of the concentration/calcination chamber. The cylindrical shape seems to be the simplest, best adapted and cheapest.

It is to be noted that the internal ring includes an upper portion and a projecting lower portion 250 which is in contact with the upper or lower plate connected to the earth (negative pole) and that the outer ring is in contact with the upper or lower electrode (positive pole) when said mobile sample support is in the upper or lower position respectively.

This mounting is advantageous in that it enables the filament to be seen through the intermediate glass tube, which enables the automatic injection operations to be monitored immediately. Furthermore, this makes it possible to evaluate the long-term state of degradation or crushing of the filament. The mounting and dismantling operations of the device are simple as for dismantling it suffices to unscrew the tie rods, dismantle the other various elements and the opposite with mounting.

Maintenance is rendered easier. In particular, it is extremely simpler to change the filament, it being merely a question of dismantling the upper plate for gaining access to the mobile sample support, partially unscrewing the two screws so as to remove the thimbles of the defective filament, placing the thimbles of a replacement filament and retightening the screws. After replacing the upper plate, the device is again ready to function.

Furthermore, the mobile sample support is in definite contact with the upper electrode in the upper position and with the lower electrode in the lower position.

Figure 5:
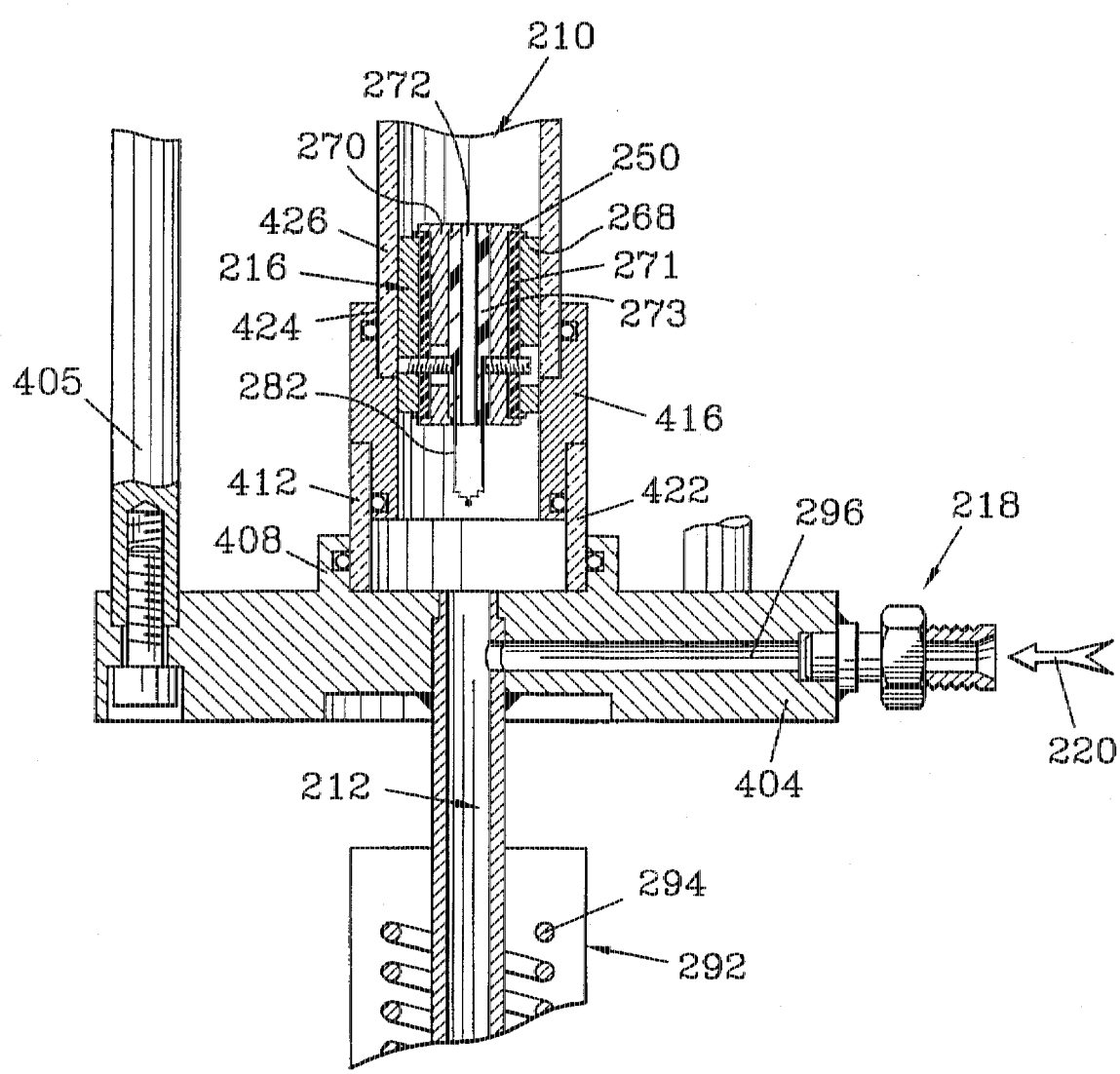
FIG. 5 is a detailed view of an embodiment variant of the electrodes with respect to the lower and intermediate tubes of the second embodiment of the device shown on FIG. 4.

So as to further improve contact of the base with the electrodes, a mounting may be provided as shown on FIG. 5 in which the electrode ensures guiding at the upper or lower position by penetrating via a peripheral countersinking into the upper 410 and lower 412 tubes.

In this second embodiment, functioning is strictly identical to the first embodiment. The controlled variation of the amount of current for the various concentration, vaporization and calcination phases is retained.

The fact of mounting the outlet stitching 298 above the mobile sample support is dictated by the proposed industrial disposition as it is easy to provide the upper plate with an internal pipe. This renders the device integrated and more compact.

The vector gas 220 introduced with a high flow results in lifting the mobile sample support from the lower position to the upper position. The effectiveness of the lifting effect is indeed reinforced by the fact that the leak point of the vector gas is located above.

What is claimed is:

1. Device for automatically injecting samples of substances solubilized or diluted in a solvent for a gaseous phase chromatographic column, the device comprising: a concentration/calcination chamber, a vaporization chamber, both vertically orientated in link with the chromatographic column, a sample support freely movable, without mechanical link, between a first position where the sample is in the concentration/calcination chamber and a second position where the sample is in the vaporization chamber, and a system for scavenging the two chambers with a vector gas, said system including means for injecting said gas between the concentration/calcination chamber and the vaporization chamber, and a valve connected to the concentration/calcination chamber opposite to the vaporization chamber.

2. Device according to claim 1, wherein the sample support includes a mobile base on which a heating filament is mounted, and electric terminals connected to said filament, and wherein the concentration/calcination chamber and vaporization chamber each include electric power units for entering into contact with the electric terminals of the base when said base is in either chamber.

3. Device according to claim 2, wherein the electric power units include means for adjusting their power.

4. Device according to claim 2, wherein the concentration/calcination chamber is orientated vertically so as to slidably receive the base subjected to gravity and mobile between an upper position and a lower position, and wherein the concentration/calcination chamber also includes means for locking/unlocking the base in the upper position.

5. Device according to claim 4, wherein the base includes a soft-iron casing and the means for locking/unlocking the base in the upper position include an electromagnet.

6. Device according to claim 4, wherein the scavenging system includes a first gas inlet stitching opening into the vaporization chamber between the concentration/calcination chamber and the chromatographic column, a second gas outlet stitching opening outside the concentration/calcination chamber, said second stitching comprising a first channel and a second channel, the first channel being equipped with a nozzle and the second channel with an electrovalve.

7. Device according to claim 6, wherein the second stitching is situated immediately under the base when the latter is in the upper position.

8. Device according to claim 4, wherein the concentration/calcination chamber includes at its upper portion an orifice for introducing a syringe needle above the base when the latter is in its upper position and wherein the base includes an opening hole orientated vertically so as to allow passage of the needle and access to the filament.

9. Device according to claim 2, wherein the electric power units include elements forming a spring working on compression.

10. Device according to claim 1, wherein the concentration/calcination chamber includes an upper plate and a lower plate, two upper and lower bases, two upper and lower tubes made of a nonconducting material, two upper and lower metallic electrodes, each including two superbores for receiving firstly the upper and lower tubes and secondly an intermediate tube, also made of a transparent nonconducting material.

* * * * *